US00PP36044P2

(12) United States Plant Patent
Warner

(10) Patent No.: US PP36,044 P2
(45) Date of Patent: Jul. 30, 2024

(54) ROSA PLANT NAMED 'CHEWARIZONA'

(50) Latin Name: *Rosa hybrida*
Varietal Denomination: CHEWARIZONA

(71) Applicant: Christopher Hugh Warner, Shropshire (GB)

(72) Inventor: Christopher Hugh Warner, Shropshire (GB)

(73) Assignee: Spring Meadow Nursery Inc., Grand Haven, MI (US)

( * ) Notice: Subject to any disclaimer, the term of this patent is extended or adjusted under 35 U.S.C. 154(b) by 0 days.

(21) Appl. No.: 18/118,433

(22) Filed: Mar. 7, 2023

(51) Int. Cl.
*A01H 5/02* (2018.01)
*A01H 6/74* (2018.01)

(52) U.S. Cl.
USPC ..... Plt./145
CPC ..... *A01H 6/749* (2018.05)

(58) Field of Classification Search
USPC ..... Plt./145
CPC ..... A01H 6/749; A01H 5/02
See application file for complete search history.

*Primary Examiner* — Keith O. Robinson
(74) *Attorney, Agent, or Firm* — Cassandra Bright

(57) ABSTRACT

A new and distinct cultivar of *Rosa* plant named 'CHEWARIZONA' is disclosed, characterized by deeply saturated yellow-amber colored double flowers, and glossy green foliage. Plants have long, repeat flowering periods, and exhibit good resistance to blackspot diseases. The new variety is a *Rosa*, normally produced as an outdoor garden or container plant.

2 Drawing Sheets

Figure 1:
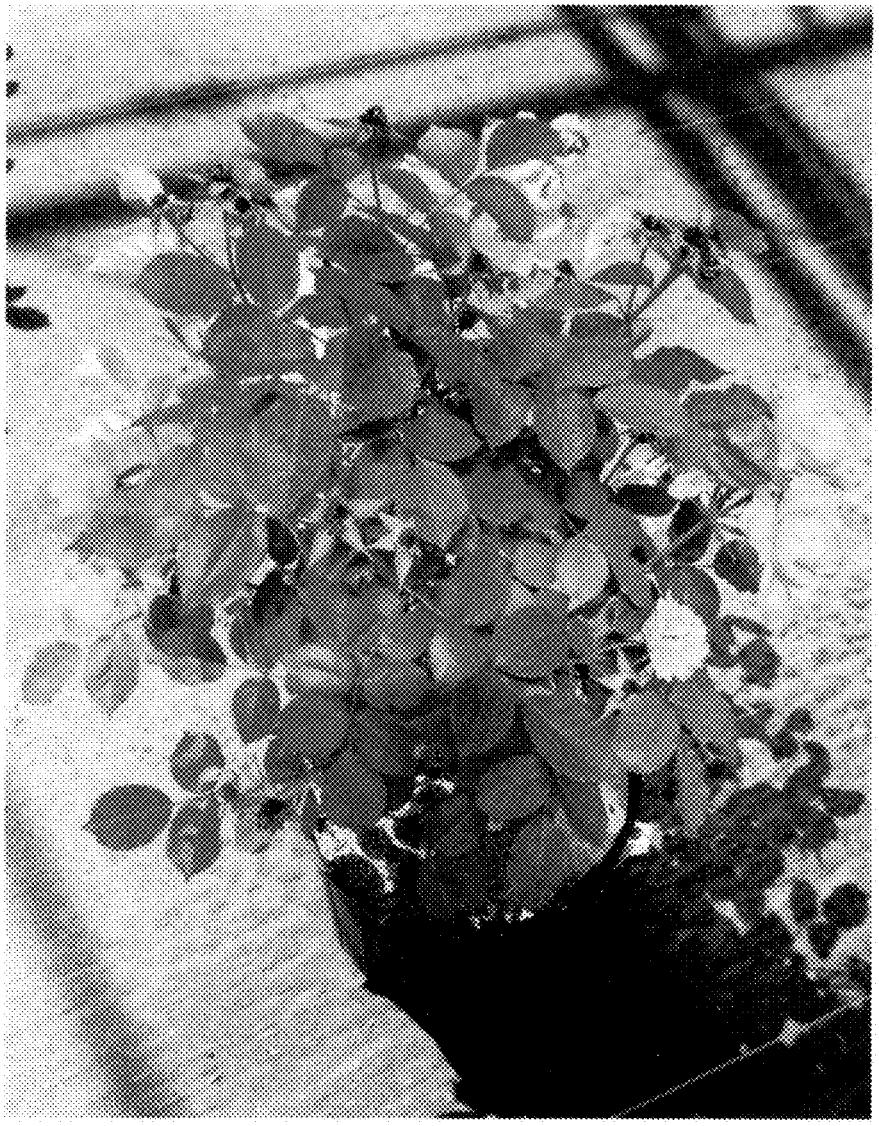

Latin name of the genus and species: *Rosa hybrida.*
Variety denomination: 'CHEWARIZONA'.

BACKGROUND OF THE INVENTION

The new *Rosa* cultivar is a product of a planned breeding program conducted by the inventor, to produce healthy floribunda rose varieties with vibrant petal color. The cross resulting in this new variety was made during May of 2014 at a nursery in Shropshire, UK.

The seed parent is the variety *Rosa* 'Kenendure', unpatented. The pollen parent is the unpatented variety *Rosa* 'Noa75800'. The new variety was selected in August of 2016 by the inventor, at the same nursery in Shropshire, UK.

Asexual reproduction of the new cultivar has been performed by softwood cuttings. This was first performed in Shropshire, UK in July of 2017, and has shown that the unique features of this cultivar are stable and reproduced true to type in more than 5 successive generations.

SUMMARY OF THE INVENTION

The cultivar 'CHEWARIZONA' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'CHEWARIZONA'. These characteristics in combination distinguish 'CHEWARIZONA' as a new and distinct *Rosa* cultivar:

1. Deeply saturated yellow-amber flower color.
2. Glossy green foliage.
3. Excellent health.

4. Medium mature size.
5. Long, repeat flowering period.

PARENT COMPARISONS

Plants of the new cultivar 'CHEWARIZONA' are similar to plants of the seed parent, in most horticultural characteristics, however, plants of the new cultivar 'CHEWARIZONA' differ in the following:

1. Flower color of the new variety is yellow-amber, while the flower color of the seed parent is lighter yellow with light pink shading.
2. Foliage of the new variety is glossier than foliage of the seed parent.
3. Plants of the new variety are more free-flowering than plants of the seed parent.
4. Plants of the new variety show improved health, while plants of the seed parent are more disease prone.
5. Flowers of the new variety are heavily double, while flowers of the seed parent are single to semi-double.

Plants of the new cultivar 'CHEWARIZONA' are similar to plants of the pollen parent in most horticultural characteristics, however, plants of the new cultivar 'CHEWARIZONA' differs in the following:

1. Flower color of the new variety is yellow-amber, while the flower color of the pollen parent is amber with a pinkish flush.
2. Petals of the new variety are less crumpled than petals of the pollen parent.
3. Plants of the new variety are more free-flowering than plants of the pollen parent.
4. Plants of the new variety show improved health, while plants of the pollen parent are more disease prone.

COMMERCIAL COMPARISON

Plants of the new cultivar 'CHEWARIZONA' can be compared to the commercial variety *Rosa* 'Korberbeni', unpatented. These varieties are similar in most horticultural characteristics, however 'CHEWARIZONA' differs in the following:

1. Flower color of the new variety is yellow-amber, while the flower color of this comparator is golden yellow.
2. Flowers of the new variety are smaller than flowers of this comparator.
3. Plants of the new variety are more free-flowering than plants of this comparator.
4. Plants of the new variety are more resistant to blackspot than plants of this comparator.
5. Flowers of the new variety have a stronger scent than flowers of this comparator.

BRIEF DESCRIPTION OF THE PHOTOGRAPHS

The accompanying photograph in FIG. 1 illustrates in full color a typical plant of 'CHEWARIZONA' grown in a 3-gallon container at approximately 1.5 years of age.

Figure 2:
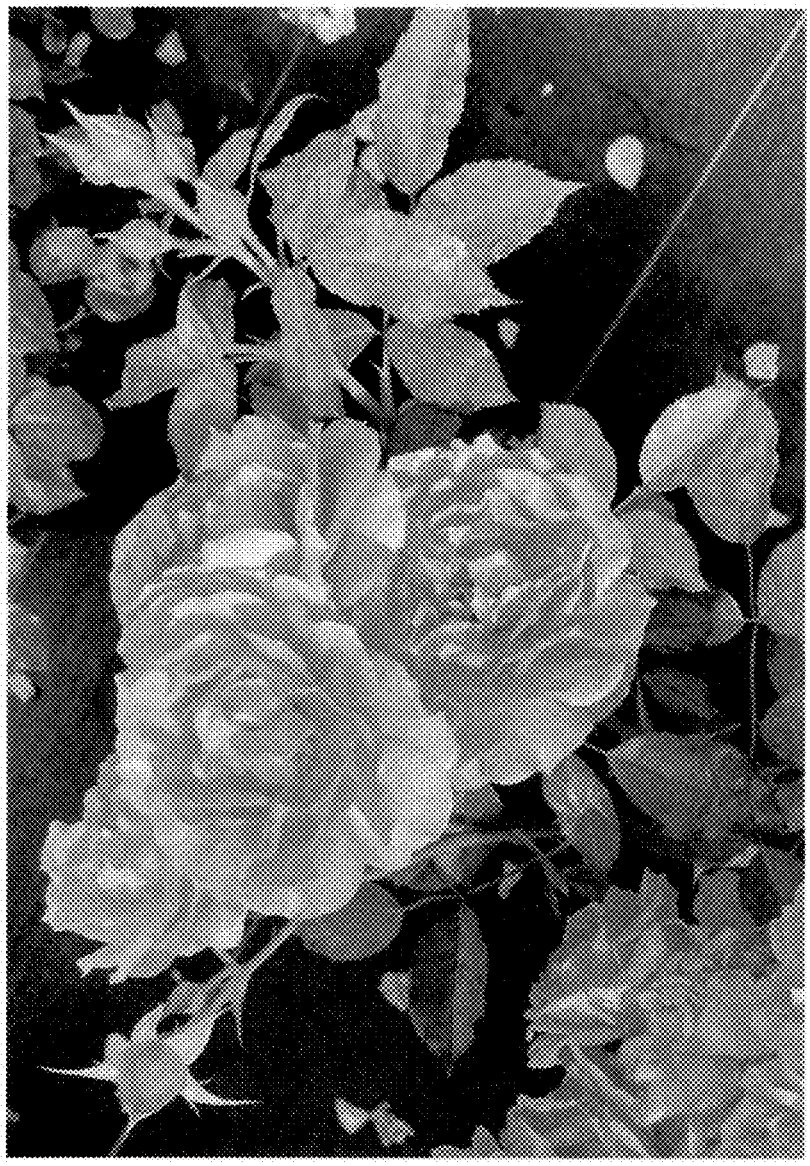

FIG. 2 illustrates in full color a close up of individual flowers and flower buds of 'CHEWARIZONA'.

The photograph was taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2015, except where general terms of ordinary dictionary significance are used. The following observations and measurements describe 'CHEWARIZONA' plants grown in a poly-greenhouse in Grand Haven, Michigan. The growing temperature ranged from approximately 18° C. to 27° C. during the day and from approximately 5° C. to 10° C. during the night. Measurements were taken in September. General light conditions were very bright, normal sunlight. Measurements and numerical values represent averages of typical plant types.

Botanical classification: *Rosa* 'CHEWARIZONA'.

PROPAGATION

Time to initiate roots: 30 days at approximately 20° C. in summer.

Time to produce a rooted cutting: 120 days at approximately 20° C. in summer.

Root description: Moderately dense, moderately branching, medium thickness, fibrous and fleshy. White in color, not accurately measured with R.H.S. chart.

PLANT

Age of plant described: 2 to 3 years.
Growth habit: Upwards.
Plant shape: Upright.
Container size: 3-gallon.
Height: 80 cm.
Plant spread: 70 cm.
Growth rate: Strong.
Branching habit: Basal, some pinching required.
Length of primary lateral branches: 60 cm.
Diameter of lateral branches: 6 mm.
Quantity branches: About 15.
Internode length: 5 cm.

Stem:
- *Appearance/shape*.—Rounded, with thorns.
- *Aspect*.—45 to 70°.
- *Strength*.—Strong.
- *Color*.—RHS Yellow-Green 144A-B.
- *Pubescence*.—None.

Thorns:
- *Quantity*.—1 to 2 per linear cm.
- *Shape*.—Acicular.
- *Apex*.—Acute.
- *Length*.—6 mm.
- *Height*.—5 mm.
- *Color, immature*.—RHS Yellow-Green 144B, tinted Greyed-Orange 176B.
- *Color, mature*.—RHS Yellow-Green 144B, tinted Greyed-Orange 176B.

FOLIAGE

Leaf:
- *Arrangement*.—Alternate.
- *Quantity*.—10 per lateral branch.
- *Length*.—14 cm, for a 5-leaflet leaf.
- *Width*.—9 cm, for a 5-leaflet leaf.
- *Pubescence*.—None.

Leaflet:
- *Quantity*.—3, 5, and 7 per leaf. Predominantly 5.
- *Terminal length*.—5 cm.
- *Terminal width*.—3.5 cm.
- *Lateral length*.—Larger Pair: 5 cm. Smaller Pair: 2.5 cm.
- *Lateral width*.—3.5 cm.
- *Shape*.—Elliptic.
- *Apex*.—Acuminate.
- *Base*.—Obtuse.
- *Margin*.—Serrate.
- *Texture*.—Glabrous, somewhat coriaceous.
- *Appearance upper surface*.—Moderately glossy.
- *Appearance lower surface*.—Matte.
- *Color*.—Young Foliage Upper Side: RHS Yellow-Green 146A. Young Foliage Under Side: RHS Yellow-Green 146B. Mature Foliage Upper Side: RHS Yellow-Green 146A. Mature Foliage Under Side: RHS Yellow-Green 146B.
- *Venation*.—Type: Pinnate. Color, Upper Side: RHS Yellow-Green 144C. Color, Under Side: RHS Yellow-Green 144C.

Petiole:
- *Leaf*.—Length: 9 cm. Diameter: 2 mm. Texture: Glabrous, both surfaces. Color: Upper Surface: RHS Yellow-Green 144C, tinted Greyed-Orange 176B. Lower Surface: RHS Yellow-Green 144C.
- *Leaflet*.—Length: 1 mm. Diameter: 1 mm. Texture: Glabrous, both surfaces. Color: Upper Surface: RHS Yellow-Green 144C, tinted Greyed-Orange 176B. Lower Surface: RHS Yellow-Green 144C.

Stipule:
- *Quantity*.—2.
- *Shape*.—Linear.
- *Apex*.—Acute.
- *Base*.—Truncate.
- *Margin*.—Serrulate.
- *Length*.—1 cm.
- *Width*.—1 mm.

*Texture*.—Glabrous, somewhat coriaceous, both surfaces.
*Color*.—Upper Surface: RHS Yellow-Green 146A. Lower Surface: RHS Yellow-Green 146B.
Durability to stress: Excellent.

FLOWER

Natural flowering season: Spring through summer (May-July).
Flower arrangement: Large sprays of multiple (often 3-6) flowers at terminal ends of lateral branches.
Flowers per spray: 3 to 6.
Quantity of sprays: 1 to 2 per lateral stem.
Spray height: 15 cm.
Spray width: 20 cm.
Flower:
*Form*.—Double, whorled.
*Diameter*.—9 cm.
*Depth*.—3 cm.
*Shape*.—Round whorl.
*Aspect*.—Upright.
*Persistence*.—Self-cleaning.
*Profile, lower part*.—Concave.
Bud:
*Shape*.—Ovate/egg-shaped.
*Length*.—1.5 cm.
*Diameter*.—1 cm.
*Color*.—Near RHS Yellow-Green 144B.
Petals:
*Appearance*.—Soft, ruffled, vibrantly colored.
*Arrangement*.—Double whorl.
*Quantity*.—35 to 40.
*Length*.—Outer Whorl: 4 cm. Inner Whorl: 3 cm.
*Width*.—Outer Whorl: 3.5 cm. Inner Whorl: 2.5 cm.
*Shape*.—Obovate.
*Margin*.—Entire.
*Apex*.—Obtuse to cuspidate.
*Fused*.—No.
*Texture*.—Silky.
*Color*.—When Opening: Upper Surface: RHS Yellow 11A at base transitioning to Orange 28D toward tip. No distinctive basal spot, color transition. Lower Surface: RHS Yellow 11A at base transitioning to Orange 28D toward tip. No distinctive basal spot, color transition. Fully Opened: Upper Surface: RHS Yellow 11A at base transitioning to Orange 24C toward tip. No distinctive basal spot, color transition. Lower Surface: RHS Yellow 11A at base transitioning to Orange 24C toward tip. No distinctive basal spot, color transition.
Petaloids:
*Appearance*.—Folded, irregular, crescent shaped.
*Arrangement*.—Whorl.
*Quantity*.—10 to 15.
*Shape*.—Irregular.
*Margin*.—Entire.
*Length*.—3 cm.
*Width*.—1.5 cm.
*Color, immature*.—RHS Yellow 11A at base transitioning to Orange 24C toward tip.
*Color, mature*.—RHS Yellow 11A at base transitioning to Orange 24C toward tip.
Sepals:
*Appearance*.—Recurve toward stem.
*Arrangement*.—Stellate.
*Shape*.—Triangular.
*Quantity*.—5.
*Length*.—3 cm.
*Width*.—1 cm.
*Apex*.—Sharply acuminate. Weak sepal extensions.
*Base*.—Fused.
*Margin*.—Entire.
*Texture*.—Rough, somewhat pubescent.
*Color*.—Immature, upper side: RHS Green 138B. Immature, under side: RHS Yellow-Green 144B. Mature, upper side: RHS Green 138B. Mature, under side: RHS Yellow-Green 144B.
Calyx:
*Shape*.—Collar-like with recurved sepals arranged in a whorl.
*Length*.—2.5 cm.
*Diameter*.—2 cm.
Peduncle:
*Length*.—5.5 cm.
*Diameter*.—3 mm.
*Angle*.—45°.
*Strength*.—Strong.
*Color*.—RHS Yellow-Green 144B.
*Texture*.—Prickly.
Fragrance: Sweet and floral, mild to moderate intensity.

REPRODUCTIVE ORGANS

Stamens:
*Quantity*.—About 80.
*Filament length*.—About 6 mm.
*Filament color*.—RHS Yellow-Orange 15A.
Anthers:
*Length*.—2 mm.
*Shape*.—Club-like, basifixed.
*Color*.—RHS Yellow-Orange 15A.
*Pollen*.—Sparse. Colored near Yellow-Orange 15D.
Pistil:
*Quantity*.—About 40.
*Length*.—4 mm.
*Stigma shape*.—Rounded.
*Stigma color*.—RHS Yellow-Orange 15A.
*Style length*.—3 mm.
*Style color*.—RHS Red 48A near stigma; White 155A near base.
*Receptacle*.—Height: 5 mm. Diameter: 7.5 mm. Shape: Orbicular. Texture: Glabrous. Color: RHS Yellow-Green 144A.

OTHER CHARACTERISTICS

Seeds and fruits: Not observed.
Disease/pest resistance: Very good resistance to powdery mildew (*Sphaerotheca pannosa* var. *rosae*), and blackspot (*Diplocarpon rosae*).
Temperature tolerance: Tolerant from −31° C. to 38° C.

What is claimed is:

1. A new and distinct cultivar of *Rosa* plant named 'CHEWARIZONA' as herein illustrated and described.

* * * * *